United States Patent
Doi et al.

[11] Patent Number: 5,889,030
[45] Date of Patent: Mar. 30, 1999

[54] METHOD FOR STABILIZING PRANOPROFEN AND STABLE LIQUID PREPARATION OF PRANAPROFEN

[75] Inventors: Koji Doi, Kobe; Hisako Sawa, Otsu; Yoshie Ozaki, Kobe; Yoshiyuki Kimura, Kakogawa, all of Japan

[73] Assignees: Senju Pharmaceutical Co., Ltd.; Yoshitomi Pharmaceutical Industries, Ltd., both of Osaka, Japan

[21] Appl. No.: 873,924

[22] Filed: Jun. 12, 1997

Related U.S. Application Data

[62] Division of Ser. No. 404,102, Mar. 14, 1995.

[51] Int. Cl.$^6$ .................................................... A61K 31/44
[52] U.S. Cl. ........................ 514/350; 514/912; 514/913; 514/914; 514/915; 428/36.91
[58] Field of Search ..................... 514/350, 912, 514/913, 914, 915; 428/36.9, 36.91, 36.92

[56] References Cited

U.S. PATENT DOCUMENTS

| | | | |
|---|---|---|---|
| 4,525,348 | 6/1985 | Arizono et al. | 424/81 |
| 4,607,038 | 8/1986 | Ogata et al. | 514/291 |
| 5,110,492 | 5/1992 | Cherng-Chyi et al. | 514/413 |
| 5,414,011 | 5/1995 | Fu et al. | 514/413 |

FOREIGN PATENT DOCUMENTS

| | | |
|---|---|---|
| 0 258 865 | 3/1988 | European Pat. Off. . |
| 0 471 084 A1 | 2/1992 | European Pat. Off. . |
| 2 839 752 | 5/1979 | Germany . |
| 2 007 091 | 5/1979 | United Kingdom . |
| 86/06629 | 11/1986 | WIPO . |
| 92/20376 | 11/1992 | WIPO . |

OTHER PUBLICATIONS

Patent Abstracts of Japan, unexamined applications, C field, vol. 10 No. 318, Oct. 29, 1986, p. 140 C 381 of JP–A–61 130 222.

Chemical Abstracts, vol. 118, 1993 No. 118:66887f (Abstract of Reference AD).

Chemical Abstracts, vol. 105, 1986, No. 105: 158837z.

*Primary Examiner*—Jose'G. Dees
*Assistant Examiner*—Michael A. Williamson
*Attorney, Agent, or Firm*—Wenderoth, Lind & Ponack, L.L.P.

[57] ABSTRACT

A method for stabilizing pranoprofen, comprising placing an aqueous solution of pranoprofen in coexistence with an antioxidant, or placing an aqueous solution of pranoprofen under the conditions of limited supply of oxygen, and a stable aqueous preparation of pranoprofen, comprising pranoprofen and an antioxidant. According to the present invention, the decomposition of pranoprofen in an aqueous solution of pranoprofen is remarkably suppressed. In particular, pranoprofen becomes stable to light, thus permitting long-term preservation of an aqueous solution, specifically a liquid preparation, of pranoprofen.

4 Claims, No Drawings

METHOD FOR STABILIZING PRANOPROFEN AND STABLE LIQUID PREPARATION OF PRANAPROFEN

This is a divisional application of Ser. No. 08/404,102, filed Mar. 14, 1995.

BACKGROUND OF THE INVENTION

1. Field of the Invention

The present invention relates to a method for stabilizing pranoprofen having anti-inflammatory activity, in an aqueous solution of pranoprofen, and to a liquid preparation comprising, as an active ingredient, pranoprofen which is stabilized by adding an antioxidant.

2. Description of Related Art

Pranoprofen having a chemical name of α-methyl-5H-[1]benzopyrano[2,3-b]pyridine-7-acetic acid exhibits prominent anti-inflammatory action, analgesic action and antipyretic action. It is a non-steroidal anti-inflammatory drug having a wider safety margin, and is commercially available by the product name of Niflan (trademark). The properties and production method thereof are described in U.S. Pat. No. 3,931,295.

There has also been proposed an eye drop containing pranoprofen as an anti-inflammatory active ingredient and boric acid as an isotonizing agent, as being useful for, in particular, herpesvirus eye diseases (U.S. Pat. No. 4,607,038).

However, pranoprofen is unstable in an aqueous solution state, particularly to light, and is gradually decomposed during long-term preservation.

It is therefore an object of the present invention to provide a method for stabilizing pranoprofen in an aqueous solution state.

Another object of the present invention is to provide an aqueous solution of pranoprofen, wherein decomposition of pranoprofen is suppressed.

SUMMARY OF THE INVENTION

According to the present invention, it has now been found that decomposition of pranoprofen can be markedly suppressed by placing an aqueous solution of pranoprofen in coexistence with an antioxidant, or placing an aqueous solution of pranoprofen under the conditions of limited supply of oxygen.

That is, the present invention and preferable modes thereof are as follows.

(1) A method for stabilizing pranoprofen, comprising placing an aqueous solution of pranoprofen in coexistence with an antioxidant.

(2) A method for stabilizing pranoprofen according to (1), comprising adding an antioxidant to an aqueous solution of pranoprofen.

(3) A method for stabilizing pranoprofen according to (2), comprising adding an antioxidant at a ratio to pranoprofen of 0.0002–5.0 by weight.

(4) A method for stabilizing pranoprofen according to (1), comprising sealing an aqueous solution of pranoprofen in a container formed from a material comprising an antioxidant.

(5) A method for stabilizing pranoprofen according to (4), comprising adding an antioxidant to a material of the container at a ratio to the material of 0.0001–0.005 by weight.

(6) A method for stabilizing pranoprofen according to (4), wherein the container is made of polypropylene.

(7) A method for stabilizing pranoprofen according to (2), wherein the antioxidant is at least one compound selected from the group consisting of alkylphenols, benzopyran derivatives, sodium thiosulfate and amino acids.

(8) A method for stabilizing pranoprofen according to (7), wherein the alkylphenol is at least one compound selected from the group consisting of dibutylhydroxytoluene and butylhydroxyanisole.

(9) A method for stabilizing pranoprofen according to (7), wherein the benzopyran derivative is at least one member selected from the group consisting of L-ascorbic acid 2-[3,4-dihydro-2,5,7,8-tetramethyl-2-(4,8,12-trimethyltridecyl)-2H-1-benzopyran-6-yl-hydrogen phosphate] and salts thereof.

(10) A method for stabilizing pranoprofen according to (7), wherein the amino acid is at least one member selected from the group consisting of methionine, tryptophan and histidine.

(11) A method for stabilizing pranoprofen according to any one of (4)–(6), wherein the antioxidant is at least one alkylphenol.

(12) A method for stabilizing pranoprofen according to (11), wherein the alkylphenol is at least one member selected from the group consisting of dibutylhydroxytoluene and butylhydroxyanisole.

(13) A method for stabilizing pranoprofen, comprising placing an aqueous solution of pranoprofen under the conditions of limited supply of oxygen.

(14) A method for stabilizing pranoprofen according to (13), comprising sealing a container, in which an aqueous solution of pranoprofen has been sealed, in a container or enclosing the container with a sheet, together with a deoxygenating agent.

(15) A method for stabilizing pranoprofen according to (13), comprising sealing an aqueous solution of pranoprofen in a container having a low oxygen permeability or enclosing the solution with a sheet having a low oxygen permeability.

(16) A stabilizing method according to (1), wherein the aqueous solution of pranoprofen is an eye drop or a collunarium.

(17) A stabilizing method according to (13), wherein the aqueous solution of pranoprofen is an eye drop or a collunarium.

(18) A stable liquid preparation of pranoprofen, comprising pranoprofen and an antioxidant.

(19) The liquid preparation of (18), wherein the antioxidant is at least one compound selected from the group consisting of alkylphenols, benzopyran derivatives, sodium thiosulfate and amino acids.

(20) The liquid preparation of (19), wherein the alkylphenol is at least one member selected from the group consisting of dibutylhydroxytoluene and butylhydroxyanisole.

(21) The liquid preparation of (19), wherein the benzopyran derivative is at least one compound selected from the group consisting of L-ascorbic acid 2-[3,4-dihydro-2,5,7,8-tetramethyl-2-(4,8,12-trimethyltridecyl)-2H-1-benzopyran-6-yl-hydrogen phosphate] and salts thereof.

(22) The liquid preparation of (19), wherein the amino acid is at least one member selected from the group consisting of methionine, tryptophan and histidine.

(23) The liquid preparation of (18), comprising an antioxidant at a ratio to pranoprofen of 0.0002–5.0 by weight.

(24) The liquid preparation of (18), which is an eye drop.

(25) The liquid preparation of (18), which is a collunarium.

DETAILED DESCRIPTION OF THE INVENTION

The first mode of the stabilizing method of the present invention is placing an aqueous solution of pranoprofen in coexistence with an antioxidant, which is realized by, for example, (i) adding an antioxidant to an aqueous solution of pranoprofen (Mode I) or (ii) sealing an aqueous solution of pranoprofen in a container formed from a material comprising an antioxidant (Mode II). The Modes I and II may be used in combination.

The antioxidant to be used in Mode I includes, for example, alkylphenols, benzopyran derivatives, sodium thiosulfate and amino acids.

Examples of alkylphenol include dibutylhydroxytoluene (BHT), butylhydroxyanisole (BHA), n-propyl gallate and catechol, with preference given to BHT and BHA.

Examples of benzopyran derivative include tocopherol, tocol, L-ascorbic acid 2-[3,4-dihydro-2,5,7,8-tetramethyl-2-(4,8,12-trimethyltridecyl)-2H-1-benzopyran-6-yl-hydrogen phosphate] and salts thereof, with preference given to L-ascorbic acid 2-[3,4-dihydro-2,5,7,8-tetramethyl-2-(4,8,12-trimethyltridecyl)-2H-1-benzopyran-6-yl-hydrogen phosphate] potassium salt ($EPC-K_1$).

Amino acid is, for example, methionine, tryptophan or histidine, with preference given to methionine and tryptophan.

When an antioxidant is added to an aqueous solution of pranoprofen according to Mode I, the antioxidant is generally added at a ratio to pranoprofen of 0.0002–5.0 by weight, preferably 0.002–2.5 by weight.

When an aqueous solution of pranoprofen is sealed in a container formed from a material comprising an antioxidant, according to Mode II, the container is, for example, generally a plastic container such as the one composed of polyolefin [e.g. polyethylene (PE) and polypropylene (PP)], with preference given to the one composed of PP.

An antioxidant is added to the material of the container at a ratio to the material of, for example, 0.0001–0.005 by weight, preferably 0.0005–0.005 by weight.

In the Mode II, the antioxidant to be used is, for example, a phenol such as alkylphenol, alkyldiphenol or thiobisalkylphenol.

Examples of alkylphenol include dibutylhydroxytoluene (BHT), butylhydroxyanisole (BHA), n-propyl gallate, stearyl β-(3,5-di-t-butyl-4-hydroxyphenyl)propionate, tetrakis[3-(3,5-di-tert-butyl-4-hydroxyphenyl) propionyloxymethyl]methane, 1,3,5-tris(3,5-di-tert-butyl-4-hydroxybenzyl)-1H,2H,3H-triazine-2,4,6-trione, 1,3,5-tris [(3,5-di-tert-butyl-4-hydroxybenzyl)-2,4,6-trimethyl] benzene and 3,9-bis[2-(3-(3-tert-butyl-4-hydroxy-5-methylphenyl)propionyloxy)-1,1-dimethylethyl]-2,4,8,10-tetraoxaspiro[5.5]undecane, with preference given to BHT and BHA.

Examples of alkyldiphenol include 2,2'-methylenebis(4-methyl-6-tert-butylphenol), 4,4'-butylidenebis(2-tert-butyl-5-methylphenol) and 2-tert-butyl-6-(3-tert-butyl-2-hydroxy-5-methylbenzyl)-4-methylphenyl acrylate.

Examples of thiobisalkylphenol include 4,4'-thiobis(2-tert-butyl-5-methylphenol).

The second mode of the stabilizing method of the present invention is placing an aqueous solution of pranoprofen under the conditions of limited oxygen supply. For example, a container containing an aqueous solution of pranoprofen sealed therein is sealed in another container or enclosed with a sheet in coexistence with a deoxygenating agent (Mode III), or an aqueous solution of pranoprofen is sealed in a container having a low oxygen permeability, or enclosed with a sheet having a low oxygen permeability (Mode IV).

In the Mode III, the container for sealing an aqueous solution of pranoprofen is subject to no particular limitation as long as it can seal an aqueous solution of pranoprofen, and is preferably exemplified by a container formed from a material containing an antioxidant, such as those exemplified for the above-mentioned Mode II, and a container having a low oxygen permeability to be mentioned below.

The deoxygenating agent to be used in Mode III is exemplified by iron powder, iron oxide, ascorbic acid and catechol, with preference given to iron oxide. The deoxygenating agent is preferably packed in a bag etc. made of an oxygen-permeable material and put to use.

The container and the sheet to enclose a container, in which an aqueous solution of pranoprofen has been sealed, together with a deoxygenating agent according to Mode III, are not subject to any particular limitation as long as they can enclose both the container, in which an aqueous solution of pranoprofen has been sealed, and a deoxygenating agent in such a manner that the outside air is shut off from them. Examples of the container include plastic containers and glass containers, and examples of the sheet include plastic sheets and aluminum sheets. The materials for such containers and sheets may contain an antioxidant, as exemplified in the above-mentioned Mode II, or may have a low oxygen permeability as discussed below. Also, an antioxidant may be added to an aqueous solution of pranoprofen in Mode III.

The container and the sheet having low oxygen permeability, which are to be used in Mode IV, are preferably made from a material having an oxygen permeability of not more than 120 cc/m$^2$·24 hr·atom [20° C.·90% relative humidity (RH), thickness of material 25 μm], preferably not more than 70 cc/m$^2$·24 hr·atom (20° C.·90% RH, thickness of material 25 μm), such as those made from acrylonitrile resins [e.g. acrylonitrile styrene (AS) and acrylonitrile butadiene styrene (ABS)] and polyethylene terephthalate (PET), with particular preference given to those made from PET.

The solvent to be used to prepare a liquid preparation and an aqueous solution of pranoprofen of the present invention is exemplified by sterile purified water, in particular, distilled water for injection. The concentration of the active ingredient pranoprofen is generally 0.01–2.0 w/v %, preferably 0.05–1.0 w/v %, which is increased or decreased as appropriate according to the object of use.

The antioxidant to be used for the liquid preparation of pranoprofen of the present invention is exemplified by those mentioned for Mode I.

The liquid preparation of the present invention may further contain various additives on demand, such as buffers, isotonizing agents, solubilizing agents, preservatives, thickeners, chelating agents, pH adjusting agents and aromatic agents.

Examples of buffer include phosphate buffer (e.g. sodium dihydrogenphosphate-disodium hydrogenphosphate and potassium dihydrogenphosphate-potassium hydroxide), borate buffer (e.g. boric acid-sodium tetraborate), citrate buffer (e.g. sodium citrate-sodium hydroxide), tartrate buffer (e.g. tartaric acid-sodium tartrate), acetate buffer (e.g. acetic acid-sodium acetate), carbonate buffer (e.g. sodium carbonate-citric acid and sodium carbonate-boric acid) and amino acid (e.g. sodium glutamate and ε-aminocaproic acid).

When the liquid preparation of pranoprofen is used as an eye drop, it is preferable that borate buffer, acetate buffer or carbonate buffer be used to decrease irritation.

Examples of isotonizing agent include saccharides such as sorbitol, glucose and mannitol, polyhydric alcohols such as glycerol and propylene glycol, salts such as sodium chloride and sodium tetraborate, and boric acid.

Examples of solubilizing agent include non-ionic surfactants such as polyoxyethylenesorbitan monooleate (polysorbate 80), polyoxyethylenemonostearate, polyethylene glycol and polyoxyethylene hydrogenated castor oil.

Examples of preservative include quaternary ammonium salts such as benzalkonium chloride, benzethonium chloride and cetylpyridinium chloride, p-hydroxybenzoates such as methyl p-hydroxybenzoate, ethyl p-hydroxybenzoate, propyl p-hydroxybenzoate and butyl p-hydroxybenzoate, benzyl alcohol, phenetyl alcohol, sorbic acid and salts thereof, thimerosal, chlorobutanol and sodium dehydroacetate.

Examples of thickener include polyvinylpyrrolidone, hydroxyethylcellulose, hydroxypropylcellulose, methylcellulose, hydroxypropylmethylcellulose, carboxymethylcellulose and salts thereof.

Examples of chelating agent include disodium edetate and citric acid.

Examples of pH-adjusting agent include hydrochloric acid, citric acid, phosphoric acid, acetic acid, tartaric acid, sodium hydroxide, potassium hydroxide, sodium carbonate and sodium hydrogencarbonate.

Examples of aromatic agent include 1-menthol, borneol, camphor (e.g. dl-camphor) and eucalyptus oil.

The liquid preparation of the present invention is used as an eye drop, collunarium and the like. When used as an eye drop, its pH is generally adjusted to about 6.0–8.5, preferably about 7.0–8.0, and when used as a collunarium, its pH is generally adjusted to about 6.0–8.5, preferably about 7.0–8.0.

While the method for producing the liquid preparation of the present invention varies depending on the kind of liquid preparation, a known method for each liquid preparation can be used.

The dose of the liquid preparation of the present invention, when used, for example, as an eye drop, is an amount sufficient to effectively resolve ophthalmic inflammation, and varies depending on symptoms and the kind of inflammation. The dose is generally 5.0–1,000 μg/administration, preferably 25–500 μg/administration, which is administered 2 to 5 times a day as appropriate.

The present invention is described in more detail in the following by referring to Experimental Examples and Examples.

EXPERIMEMTAL EXAMPLE 1
[Stability test—No. 1]

A solution of 0.1 w/v % pranoprofen [boric acid, 1.6 w/v %; sodium tetraborate, appropriate amount; disodium edetate, 0.01 w/v %; benzalkonium chloride, 0.005 w/v %; polysorbate 80, 0.1 w/v %; sterile purified water, appropriate amount] was filled in 5 ml polypropylene containers manufactured by adding BHT to 0.05, 0.1 or 0.5 w/v % [oxygen permeability of 25 μm thick test sample, 3,800 cc/m$^2$·24 hr·atom (20° C.·90% RH); Gas Permeation Test Method of Plastic Film and Sheet of Japanese Industrial Standards, the equal pressure method [Japanese Standards Association, JIS Handbook, p 400, Tokyo (1991)]] and 15 ml polyethylene terephthalate containers [oxygen permeability of 25 μm thick test samples, 63 cc/m$^2$·24 hr·atom (20° C.·90% RH); Gas Permeation Test Method of Plastic Film and Sheet of Japanese Industrial Standards, the equal pressure method [Japanese Standards Association, JIS Handbook, p 400, Tokyo (1991)]], and left standing in the dark at room temperature for 36 months. The residual content of pranoprofen in the containers was determined with time by high performance liquid chromatography. The results are shown in Table 1.

TABLE 1

| | Residual content of pranoprofen (%) | | | | | |
|---|---|---|---|---|---|---|
| Container | On preparation | 3 months | 6 months | 12 months | 24 months | 36 months |
| PP (control) | 100.0 | 95.6 | 93.9 | — | 81.9 | 78.5 |
| PP-05 | 100.0 | 100.4 | 99.3 | 99.0 | 98.5 | 100.2 |
| PP-01 | 100.0 | 100.4 | 98.3 | 98.1 | 95.4 | 96.0 |
| PP-005 | 100.0 | 100.4 | 98.3 | 97.0 | 93.2 | 93.3 |
| PET | 100.0 | 99.5 | 101.0 | 100.3 | 100.8 | 99.4 |

PP: polypropylene container without BHT oxygen permeability, 3800 cc/m$^2$·24 hr·atom (20° C.·90% RH, 25 μm)
PP-05: polypropylene container containing 0.5% BHT
PP-01: polypropylene container containing 0.1% BHT
PP-005: polypropylene container containing 0.05% BHT
PET: polyethylene terephthalate container without BHT oxygen permeability, 63 cc/m$^2$·24 hr·atom (20° C.·90% RH, 25 μm)

As is evident from Table 1, superior suppression of decomposition of pranoprofen was achieved by preserving pranoprofen in the containers (PP) formed from a material containing BHT and in the container (PET) having a low oxygen permeability.

EXPERIMENTAL EXAMPLE 2
[Stability test—No. 2]

BHT or sodium thiosulfate was added to a basic formulation solution [pranoprofen, 0.1 w/v %; boric acid, 1.6 w/v %; sodium tetraborate, appropriate amount; disodium edetate, 0.01 w/v %; benzalkonium chloride, 0.005 w/v %; polysorbate 80, 0.1 w/v %; sterile purified water, appropriate amount], and the mixture was filled in 5 ml polypropylene containers. The containers were left standing in the dark at room temperature for 39 months. The residual content of pranoprofen in the containers was determined by high performance liquid chromatography. The results are shown in Table 2.

TABLE 2

| | | Residual content of pranoprofen (%) | |
|---|---|---|---|
| | Concentration | | |
| Compound added | (%) | On preparation | after 39 months |
| Control (not added) | 0 | 100.0 | 77.0 |
| BHT | 0.0004 | 100.0 | 99.6 |
| " | 0.0001 | 100.0 | 94.7 |
| sodium thiosulfate | 0.1 | 100.0 | 93.0 |

As is evident from Table 2, superior suppression of decomposition of pranoprofen was achieved by the addition of respective antioxidants.

EXPERIMENTAL EXAMPLE 3
[Stability test—No. 3]

BHT, BHA, L-ascorbic acid 2-[3,4-dihydro-2,5,7,8-tetramethyl-2-(4,8,12-trimethyltridecyl)-2H-1-benzopyran-6-yl-hydrogen phosphate] potassium salt (EPC-KI), methionine, tryptophan or histidine was added to a basic formulation solution [pranoprofen, 0.05 w/v %; boric acid, 1.6 w/v %; sodium tetraborate, appropriate amount; disodium edetate, 0.01 w/v %; benzalkonium chloride, 0.005 w/v %; polysorbate 80, 0.1 w/v %; sterile purified water, appropriate amount], and the mixture was filled in colorless 15 ml polyethylene terephthalate containers. The containers were left standing under a fluorescent lamp (20 W). When the total irradiation reached 100,000 lux·hr, the residual content of pranoprofen in the containers was determined by high performance liquid chromatography. The results are shown in Table 3.

TABLE 3

| Compound added | Concentration (%) | On preparation | Residual content of pranoprofen (%) after irradiation of 100,000 lux · hr |
|---|---|---|---|
| Control (not added) | 0 | 100.0 | 52.5 |
| BHT | 0.005 | 100.0 | 98.0 |
| " | 0.002 | 100.0 | 96.6 |
| " | 0.0002 | 100.0 | 70.8 |
| BHA | 0.002 | 100.0 | 92.8 |
| EPC-K$_1$ | 0.05 | 100.0 | 79.1 |
| " | 0.01 | 100.0 | 70.5 |
| " | 0.001 | 100.0 | 68.2 |
| methionine | 0.24 | 100.0 | 95.2 |
| tryptophan | 0.06 | 100.0 | 96.9 |
| histidine | 0.13 | 100.0 | 75.9 |

As is evident from Table 3, the decomposition of pranoprofen caused by the exposure to the light was markedly suppressed by the addition of respective antioxidants.

EXPERIMENTAL EXAMPLE 4
[Stability test—No. 4]

A solution of 0.1 w/v % pranoprofen [boric acid, 1.6 w/v %; sodium tetraborate, appropriate amount; disodium edetate, 0.01 w/v %; benzalkonium chloride, 0.005 w/v %; polysorbate 80, 0.1 w/v %; sterile purified water, appropriate amount] was filled in 5 ml polypropylene containers and the containers were tightly sealed. The containers were enclosed together with iron oxide (Ageless Z-30, manufactured by Mitsubishi Gas Chemical Company, Inc.) as a deoxygenating agent, with the use of a multi-layer film of polypropylene/poly(vinyl alcohol)/polyethylene and left standing at room temperature for 30 months. The residual content of pranoprofen in the containers was determined with time by high performance liquid chromatography. The results are shown in Table 4.

TABLE 4

| | | Residual content of pranoprofen (%) | | | |
|---|---|---|---|---|---|
| Enclosing | On preparation | 2 months | 6 months | 9 months | 30 months |
| Unenclosed | 100.0 | 95.1 | 89.4 | 92.0 | 80.3 |
| Film-enclosed (deoxygenator) | 100.0 | 98.1 | 97.6 | 97.2 | 101.0 |
| Film-enclosed (N$_2$ substitution) | 100.0 | 95.0 | 93.4 | 89.5 | 88.5 |

Containers used: polypropylene containers without BHT
Film: multi-layer film of polypropylene/poly(vinyl alcohol)/polyethylene
deoxygenating agent: iron oxide (Ageless Z-30, manufactured by Mitsubishi Gas Chemical Company, Inc.)

As is evident from Table 4, marked suppression of decomposition of pranoprofen was achieved by sealing a container, in which an aqueous solution of pranoprofen had been sealed, together with a deoxygenating agent.

EXAMPLE 1 [Eye drop]

| (1) Pranoprofen | 0.2 g |
|---|---|
| (2) Disodium hydrogenphosphate | 0.5 g |
| (3) Sodium dihydrogenphosphate | 0.1 g |
| (4) Polyoxyethylene hydrogenated castor oil 60 | 0.1 g |
| (5) Poly(vinyl alcohol) | 0.2 g |
| (6) Sodium chloride | 0.8 g |
| (7) Benzethonium chloride | 0.007 g |
| (8) BHT | 0.01 g |
| (9) Sodium hydroxide | appropriate amount |
| (10) Sterile purified water | appropriate amount |
| Total | 100 ml |

(5) was added to about 70 ml of (10) and the mixture was stirred with heating to about 70° C. for dissolution. (4) and (8) were added to this solution and the mixture was admixed until it became a uniform dispersion. The mixture was cooled to room temperature. (1), (2), (3), (6) and (7) were dissolved in this solution and pH was adjusted to 7.2 with (9). (10) was added to make the total amount 100 ml and the mixture was filled in a 5 ml PE container for an eye drop.

EXAMPLE 2 [Eye drop]

| (1) Pranoprofen | 0.4 g |
|---|---|
| (2) Sodium chloride | 0.5 g |
| (3) Polysorbate 80 | 0.15 g |
| (4) Polyethylene glycol | 0.5 g |
| (5) Citric acid | 0.2 g |
| (6) Benzalkonium chloride | 0.009 g |
| (7) Sodium thiosulfate | 0.01 g |
| (8) Sodium carbonate | appropriate amount |
| (9) Sterile purified water | appropriate amount |
| Total | 100 ml |

(1), (2), (3), (4), (5), (6) and (7) were dissolved in about 70 ml of (9) and pH was adjusted to 8.0 with (8). (9) was added to make the total amount 100 ml and the mixture was filled in a 5 ml PP container for an eye drop.

EXAMPLE 3 [Eye drop]

| (1) Pranoprofen | 0.1 g |
|---|---|
| (2) Potassium dihydrogenphosphate | 0.3 g |
| (3) Conc. glycerol | 2.6 g |
| (4) Potassium hydroxide | appropriate amount |
| (5) Disodium edetate | 0.01 g |
| (6) EPC-K$_1$ | 0.05 g |
| (7) Methyl p-hydroxybenzoate | 0.026 g |
| (8) Propyl p-hydroxybenzoate | 0.014 g |
| (9) Sterile purified water | appropriate amount |
| Total | 100 ml |

About 80 ml of (9) was heated to about 90° C. and (7) and (8) were dissolved. The mixture was cooled to room temperature. An appropriate amount of (4) was dissolved and then, (1), (2), (3), (5) and (6) were dissolved. Its pH was adjusted to 6.5 with (4). (9) was added to make the total amount 100 ml and the mixture was filled in a 10 ml polycarbonate container for an eye drop.

EXAMPLE 4 [Eye drop]

| | |
|---|---|
| (1) Pranoprofen | 0.1 g |
| (2) Boric acid | 1.6 g |
| (3) Sodium tetraborate | appropriate amount |
| (4) Disodium edetate | 0.01 g |
| (5) Polysorbate 80 | 0.15 g |
| (6) Benzalkonium chloride | 0.007 g |
| (7) Sterile purified water | appropriate amount |
| Total | 100 ml |

(1), (2), (3), (4), (5) and (6) were dissolved in about 80 ml of (7), and pH was adjusted to 7.0 with (3). (7) was added to make the total amount 100 ml and the mixture was filled in a 5 ml PP container for an eye drop, which comprised 0.5% BHT.

EXAMPLE 5 [Eye drop]

| | |
|---|---|
| (1) Pranoprofen | 0.1 g |
| (2) Boric acid | 1.6 g |
| (3) Sodium tetraborate | appropriate amount |
| (4) Disodium edetate | 0.01 g |
| (5) Polysorbate 80 | 0.15 g |
| (6) Benzalkonium chloride | 0.007 g |
| (7) Sterile purified water | appropriate amount |
| Total | 100 ml |

(1), (2), (3), (4), (5) and (6) were dissolved in about 80 ml of (7), and pH was adjusted to 7.0 with (3). (7) was added to make the total amount 100 ml and the mixture was filled in a 5 ml PP container for an eye drop. The container and iron oxide (Ageless Z-30; manufactured by Mitsubishi Gas Chemical Company, Inc.) were enclosed with a multi-layer film of polypropylene/poly(vinyl alcohol)/polyethylene.

EXAMPLE 6 [Eye drop]

| | |
|---|---|
| (1) Pranoprofen | 0.05 g |
| (2) Boric acid | 1.6 g |
| (3) Sodium tetraborate | appropriate amount |
| (4) Disodium edetate | 0.01 g |
| (5) Benzalkonium chloride | 0.005 g |
| (6) 1-menthol | 0.002 g |
| (7) dl-camphor | 0.0005 g |
| (8) Polysorbate 80 | 0.1 g |
| (9) Sterile purified water | appropriate amount |
| Total | 100 ml |

(1), (2), (3), (4) and (5) were dissolved in about 70 ml of (9). (6), (7) and (8) were admixed and uniformly dispersed in about 20 ml of (9) heated to about 60° C. This dispersion was added to the above-mentioned solution. The pH of the mixture was adjusted to 7.5 with (3) and (9) was added to make the total amount 100 ml. The mixture was filled in a 15 ml PET container for an eye drop and enclosed to avoid light.

EXAMPLE 7 [Collunarium]

| | |
|---|---|
| (1) Pranoprofen | 0.4 g |
| (2) Sodium citrate | 0.2 g |
| (3) Polysorbate 80 | 0.1 g |
| (4) Glycerol | 2.6 g |
| (5) Benzethonium chloride | 0.007 g |
| (6) Methionine | 0.24 g |
| (7) Sodium hydroxide | appropriate amount |
| (8) Sterile purified water | appropriate amount |
| Total | 100 ml |

(1), (2), (3), (4), (5) and (6) were dissolved in about 70 ml of (8), and pH was adjusted to 7.5 with (7). (8) was added to make the total amount 100 ml and the mixture was filled in a 5 ml PP container for a collunarium.

EXAMPLE 8 [Collunarium]

| | |
|---|---|
| (1) Pranoprofen | 1.0 g |
| (2) Boric acid | 1.2 g |
| (3) Sodium tetraborate | 0.8 g |
| (4) Disodium edetate | 0.01 g |
| (5) Polysorbate 80 | 0.15 g |
| (6) Benzalkonium chloride | 0.007 g |
| (7) Sodium hydroxide | appropriate amount |
| (8) Sterile purified water | appropriate amount |
| Total | 100 ml |

(1), (2), (3), (4), (5) and (6) were dissolved in about 80 ml of (8), and pH was adjusted to 7.0 with (7). (8) was added to make the total amount 100 ml and the mixture was filled in a 8 ml PE container for a collunarium. The container and iron oxide (Ageless Z-30; manufactured by Mitsubishi Gas Chemical Company, Inc.) were enclosed with a multi-layer film of polypropylene/poly(vinyl alcohol )/polyethylene.

According to the present invention, the decomposition of the active ingredient pranoprofen is remarkably suppressed. In particular, pranoprofen becomes stable to light, thus permitting long-term preservation of an aqueous solution (preparation) of pranoprofen.

What is claimed is:

1. A method for stabilizing pranoprofen, comprising sealing an aqueous solution of pranoprofen in a container formed from a mixture comprising a material for the container and at least one alkylphenol antioxidant.

2. The method of claim 1, wherein the alkylphenol is at least one member selected from a group consisting of dibutylhydroxytoluene and butylhydroxyanisole.

3. The method of claim 1, wherein the weight ratio of the antioxidant to the material is 0.0001–0.005:1.

4. The method of claim 1, wherein the container is made of polypropylene.

* * * * *

UNITED STATES PATENT AND TRADEMARK OFFICE
CERTIFICATE OF CORRECTION

PATENT NO. : 5,889,030
DATED       : March 30, 1999
INVENTOR(S) : Koji DOI et al.

It is certified that error appears in the above-identified patent and that said Letters Patent is hereby corrected as shown below:

On the Title page, item [30]:

Please insert the following Foreign Application Priority Data Information -- Japanese Patent Application No. 6-044184 filed March 15, 1994 --

Signed and Sealed this

Sixteenth Day of May, 2000

Attest:

Q. TODD DICKINSON

*Attesting Officer*          *Director of Patents and Trademarks*